United States Patent
Kreindel et al.

(10) Patent No.: US 12,397,155 B2
(45) Date of Patent: Aug. 26, 2025

(54) METHOD FOR TREATMENT OF ERECTILE DYSFUNCTION

(71) Applicant: Inmode Ltd., Yokneam (IL)

(72) Inventors: Michael Kreindel, Richmond Hill (CA); Moshe Mizrahy, Tel Aviv (IL)

(73) Assignee: Inmode Ltd., Yokneam (IL)

(*) Notice: Subject to any disclaimer, the term of this patent is extended or adjusted under 35 U.S.C. 154(b) by 447 days.

(21) Appl. No.: 18/052,276

(22) Filed: Nov. 3, 2022

(65) Prior Publication Data

US 2024/0149058 A1    May 9, 2024

(51) Int. Cl.
*A61N 1/36* (2006.01)
*A61N 1/06* (2006.01)
*A61N 1/40* (2006.01)

(52) U.S. Cl.
CPC .......... *A61N 1/36007* (2013.01); *A61N 1/06* (2013.01); *A61N 1/403* (2013.01)

(58) Field of Classification Search
None
See application file for complete search history.

(56) References Cited

U.S. PATENT DOCUMENTS

2018/0064937 A1* 3/2018 Lischinsky .............. A61N 1/36
2022/0296910 A1* 9/2022 Mizrahy ................ A61N 1/403

* cited by examiner

*Primary Examiner* — Michael W Kahelin
(74) *Attorney, Agent, or Firm* — Dekel Patent Ltd.; David Klein

(57) ABSTRACT

A method for treatment of erectile dysfunction is described using RF energy with multiple electrodes applied to the treated tissue.

9 Claims, 3 Drawing Sheets

METHOD FOR TREATMENT OF ERECTILE DYSFUNCTION

FIELD OF THE INVENTION

The invention relates to a device for treatment of erectile dysfunction by creating revascularization in a penis using deep heating.

BACKGROUND OF THE INVENTION

Erectile dysfunction is a common problem for aged male individuals. The most popular solution for these patients is PDE5 inhibitors. However, not everyone responds to the medication and not everyone is satisfied with the solution because of lack of spontaneity.

An alternative solution is using RF energy for tissue heating and improving blood circulation. U.S. Pat. No. 9,913,981 and 10,729,904 describe methods for delivering energy, non-invasively, to a penile tissue comprising at least one of tunica albuginea and penile using a plurality of RF electrode pairs externally arranged along a circumference of the penis, wherein RF electrodes in each RF electrode pair of the plurality of RF electrode pairs contact the outer skin surface of the penis at a substantially opposite sides of the penis with respect to each other.

SUMMARY

The present invention describes a method for delivery RF energy to the penile using multiple electrodes positioning along the penis length at the distance limiting RF penetration into the penile tissue more than a few millimeters. The RF current flows between the electrodes positioned on the penis surface close to each other. In contrast with the prior art, in the present invention, only a superficial part of the penis is treated to increase collagen production in tunica and increase blood circulation in corpora spongiosa, while the internal structure including the urethra and large vessels is not affected.

Each electrode may have a capacitive contact with the tissue. The electrode may be covered by a dielectric material isolating the electrode from direct contact with tissue. RF energy may be delivered through the displacement current in the dielectric layer. This method allows avoiding direct galvanic contact between the electrode and tissue, and isolates the patient from the electronic circuit. The method may include using a simple inexpensive cover applied between the electrode and patient to avoid cross-contamination.

The RF current can be applied between two bi-polar electrodes, between a few pairs of bipolar electrodes or alternatively between multiple electrodes where RF current flows from the electrode having one polarity to the multiple electrodes having opposite polarity.

The frequency of RF current is high enough to allow the current to be delivered through the dielectric film from the electrode to the tissue.

RF frequency of 400 kHz or higher may be used to deliver energy efficiently to the tissue. The impedance of the dielectric layer is in opposite proportion to the frequency of RF energy. A dielectric film with a thickness of 100 microns and an area of 10 cm$^2$ has an impedance of about 720 Ohm at 1 MHz and 360 Ohm at 2 MHz.

The RF electrodes can be located on an applicator applied to the treatment area. A conductive gel can be used for better coupling between the penis and the applicator. The applicator may comprise one or more thermal sensors to monitor tissue surface temperature during the treatment. A thermistor, thermocouple or optical sensors can be used as the temperature sensor. Thermal camera can be used to monitor the treatment. The applicator may include a disposable part which contacts the patient and a reusable part.

The applicator may have a semi-cylindrical concave surface which is applied to the larger surface area of the penis.

In one embodiment, multiple electrode units can be applied to the treatment area and RF energy can be switched between them instead of moving the RF unit over the treatment area. The vibration can be applied to stimulate blood circulation and minimize thermal discomfort. The method can be used not only for erectile dysfunction (ED) treatment but for any application where collagen growth stimulation and improvement of blood circulation is required. For example, although not related to ED treatment, wrinkle treatment and skin tightening are potential applications for this method.

RF energy may be delivered slowly enough to allow heat conductivity to homogenize the thermal effect around the electrodes and over the treated volume. Slow buildup of the temperature allows more reliable measurements of the tissue temperature.

The disposable part can be designed as a flexible PCB having a conductive layer on one side and a non-conductive layer that contacts the tissue.

Alternatively, the disposable part can be made from a metal sheet shaped for better contact with penile tissue and coated with a dielectric material. The dielectric material is biocompatible for contacting the patient.

In another embodiment, electrodes can be made from a conductive material, such as metal, composite materials or plastic coated with a metalized layer.

Each of the electrodes can be structured from a few elements for adjusting the contact surface. A spring loading mechanism can be used for better contact of the electrode with the patient.

The device may include an RF generator, an applicator, a user interface, a microprocessor and a circuit for monitoring RF parameters, such as RF current, RF voltage, RF power and tissue impedance.

The microprocessor may have software for controlling delivery of RF energy and adjusting RF output according to measured RF parameters and tissue temperature.

The applicator can be connected with a harness to the console to be attached to the patient. Alternatively, the applicator can be part of the console, and the patient sits on the device above the applicator coupled to the treated area.

The RF current heats the tissue to stimulate revascularization, collagen production and blood circulation without thermal coagulation of the tissue. The heating temperature must be below 50° C. for peak temperature and below 45° C. for the average temperature.

The treatment attendant can move the applicator over the treatment area creating uniform temperature distribution and maintaining desired temperature during the treatment time.

Preferred direction of movement is along the penis axis and preferred orientation of the electrode is transversal to the movement direction. Perineum area also can be treated to improve the treatment results.

The treatment time and number of treatments can be different depending on the severity of the problem.

The applicator may be coupled to the patient, and the treatment time and required tissue temperature may be set by the medical professional, and the medical professional does not have to be in the room with the patient during the treatment. The treatment time can be varied from 5 min up to 90 min. Patient may have access to a button that pauses the treatment in case of discomfort or emergency.

There is provided in accordance with a non-limiting embodiment of the invention a method for treating erectile dysfunction including applying RF energy in combination with other type of heating including optical energy, ultrasound energy, microwave energy.

There is provided in accordance with a non-limiting embodiment of the invention a method for treating erectile dysfunction including stretching penile tissue while heating the penile tissue with RF energy, wherein a combination of the stretching and the thermal energy improves blood flow in the penile tissue to treat erectile dysfunction of the penile tissue, wherein the stretching opens compressed blood vessels and the penile tissue is heated to a heated temperature above normal body temperature. The stretching may be created by applying negative pressure to the penile tissue.

The use of negative pressure enables filling the penile tissue with blood and increasing its conductivity for RF current.

BRIEF DESCRIPTION OF THE DRAWINGS

In the accompanying drawings.

DETAILED DESCRIPTION

Figure 1:
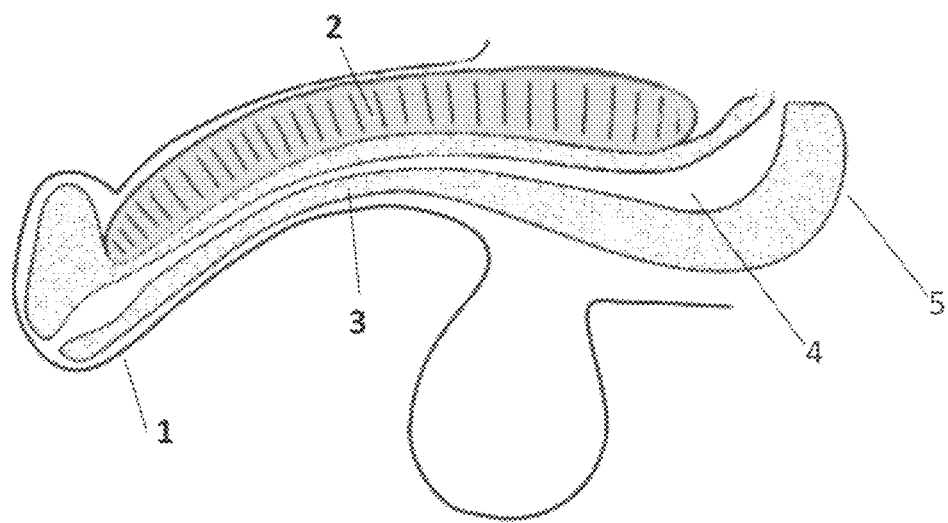
FIG. 1 is a schematic illustration of penis anatomy.

Referring to FIG. 1, a penile structure comprises outer part with distal end 1. The corpora cavernosa 2, the corpus spongiosum 3 and the urethra 4 extend along the length of the penis outside and inside the human body. The bulb 5 of the penis is located deep inside the body in proximity to the skin surface near the scrotum.

Figure 2:
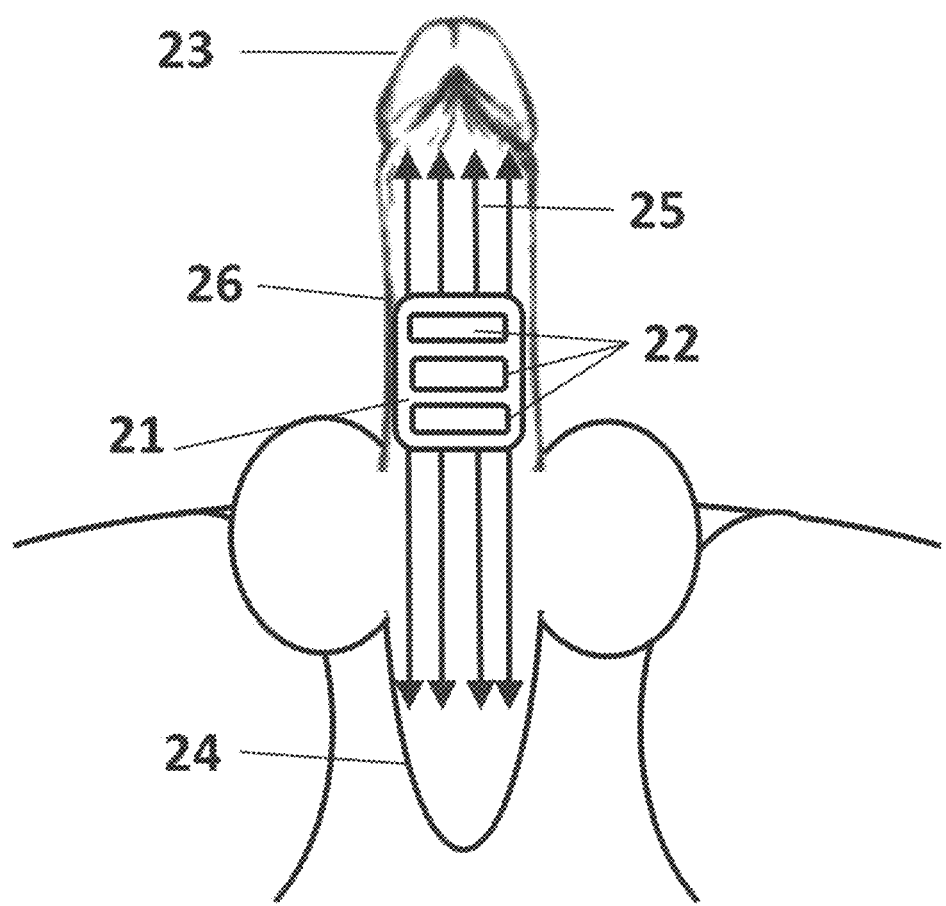
FIG. 2 is an illustration of treatment area with attached applicator.

FIG. 2 shows a bottom view of the patient in which an RF applicator 21 with multiple electrodes 22 has been applied to a treated surface 26. The applicator 21 is moved substantially along the penis axis from the head of penis 23 toward the perineum area 24 and back. The arrows 25 show a preferred direction of applicator movement. The applicator may be moved radially to heat all area of penis uniformly.

Figure 3:
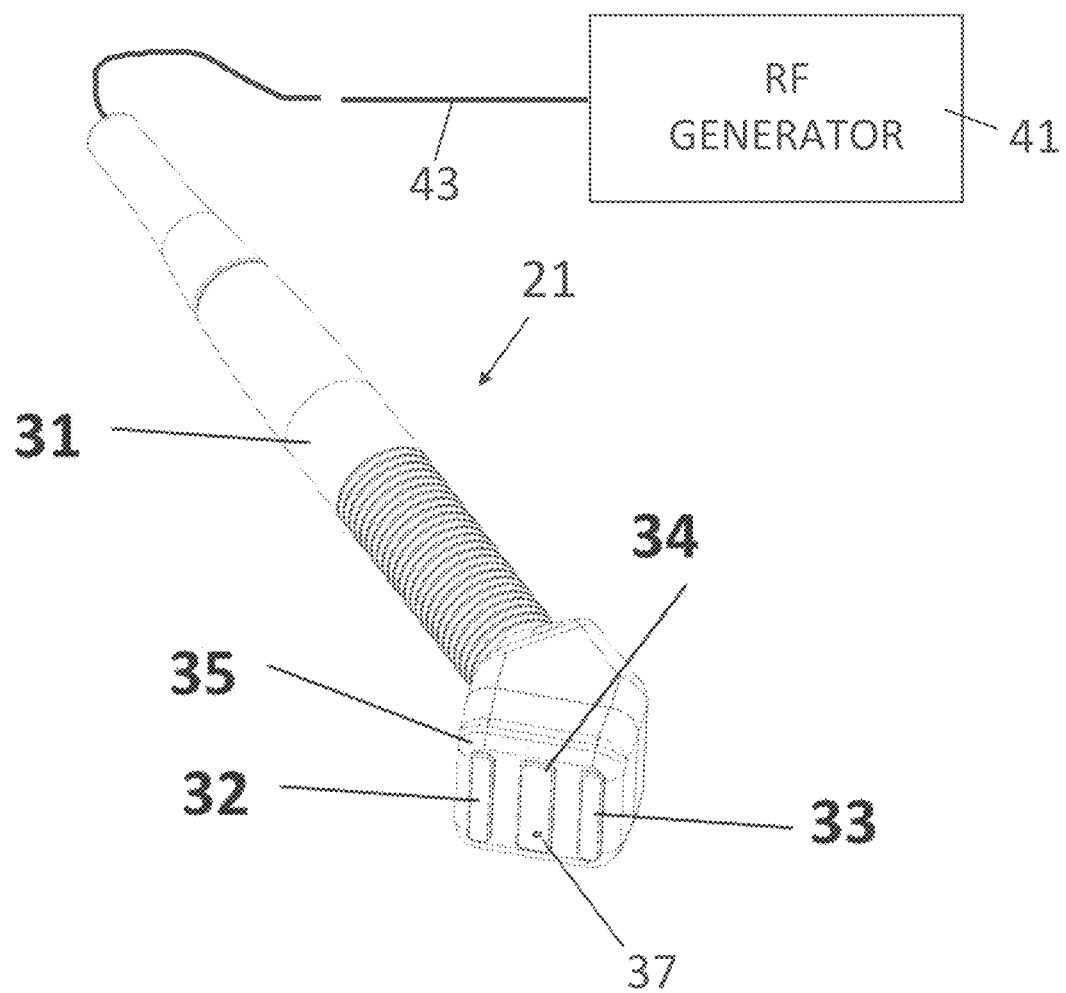
FIG. 3 is a schematic illustration of RF applicator.

FIG. 3 illustrates a preferred embodiment of the RF applicator 21. The applicator 21 may include a handle 31 and a treatment tip 35. The applicator may be connected to an RF generator 41 generating RF energy which is delivered to the applicator 21 via a cable 43. The treatment tip comprises three electrodes 32, 33, and 34. The central electrode 34 has one polarity while side electrodes 32 and 33 have opposite polarity. A thermal sensor may be embedded at least into the central electrode 34.

Heating of the penile tissue improves local blood circulation and strengthens collagen of intima of the penis.

Non-limiting parameters for the device of the invention are as follows:

RF average power is in the range of 2 W up to 75 W.

The RF frequency may be above 0.3 MHz and 5 MHz or higher for electrodes with capacitive coupling.

The treatment time may be in the range of 5 min to 90 min.

The distance between electrodes may be up to 10 mm.

In contrast to the above-described embodiment, different shapes and structure of electrodes can be used.

The invention claimed is:

1. A method for treating erectile dysfunction comprising:
applying an applicator with two or more electrodes to a penis, wherein one of said electrodes is located closer to a bulb of the penis and another of said electrodes is located closer to a distal end of the penis;
applying RF current between two or more of said electrodes such that RF current flows between electrodes substantially along a penile surface and substantially no RF current flows to a urethra of the penis; and
controlling said RF current to reach and maintain a desired tissue temperature on said penile surface.

2. The method according to claim 1, wherein said applicator is moved along the penis to create a uniform temperature distribution.

3. The method according to claim 1, wherein the desired tissue temperature is in a range of 40° C. to 50° C.

4. The method according to claim 1, wherein said applicator has three parallel electrodes wherein a central electrode has one polarity while side electrodes have an opposite polarity.

5. The method according to claim 1, wherein said applicator is moved from a penis bulb to a penis head to heat an entire length of the penis.

6. The method according to claim 1, wherein said heating of the penile tissue improves local blood circulation and strengthens collagen of intima of the penis.

7. The method according to claim 1, comprising heating the penis for 5 minutes or longer.

8. The method according to claim 1, wherein a temperature sensor is embedded at least in one of the electrodes to control the tissue temperature.

9. The method according to claim 8, wherein RF energy is controlled according to the tissue temperature measurements to maintain the desired tissue temperature.

* * * * *